United States Patent
Höbel

(10) Patent No.: US 6,333,964 B1
(45) Date of Patent: Dec. 25, 2001

(54) METHOD AND IMAGE PICKUP SYSTEM FOR MEASURING AN IMAGING RADIATION DOSE DURING PICKUP OF A RADIATION IMAGE OF A SUBJECT

(75) Inventor: Peter Höbel, Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/446,281

(22) PCT Filed: Jun. 17, 1998

(86) PCT No.: PCT/DE98/01662

§ 371 Date: Dec. 17, 1999

§ 102(e) Date: Dec. 17, 1999

(87) PCT Pub. No.: WO98/58244

PCT Pub. Date: Dec. 23, 1998

(30) Foreign Application Priority Data

Jun. 18, 1997 (DE) .............................. 197 25 852
Jun. 19, 1997 (DE) .............................. 197 26 060

(51) Int. Cl.⁷ .................................................. H05G 1/64
(52) U.S. Cl. .......................................... 378/98.7; 378/108
(58) Field of Search .................... 378/98.7, 108, 378/97

(56) References Cited

U.S. PATENT DOCUMENTS

| | | |
|---|---|---|
| 4,963,746 | 10/1990 | Morgan et al. . |
| 5,574,765 | 11/1996 | Hassler et al. . |
| 5,751,783 * | 5/1998 | Granfors et al. ..................... 378/108 |
| 6,151,383 * | 11/2000 | Xue et al. ............................ 378/108 |

OTHER PUBLICATIONS

"Bildgebende Systeme für die medizinische Diagnostik," Morneburg (1995) pp. 282–283.

* cited by examiner

Primary Examiner—Craig E. Church
(74) Attorney, Agent, or Firm—Schiff Hardin & Waite

(57) ABSTRACT

In a method and apparatus for measuring the imaging dose in the framework of the registration of a radiation image of a subject, particularly of an x-ray image, a radiation source is employed for generating radiation, a solid-state radiation detector is employed for image pickup and a sensor is employed for calculating the imaging dose, and a radiation detector on a semiconductor base that lies behind the solid-state radiation detector with reference to the direction of the radiation incident onto the solid-state radiation detector is employed, for measuring radiation penetrating through the solid-state radiation detector. The radiation sensor emits an output signal that represents the measured radiation, and the imaging dose at a location in front of the solid-state radiation detector is determined based on the output signal.

16 Claims, 5 Drawing Sheets

METHOD AND IMAGE PICKUP SYSTEM FOR MEASURING AN IMAGING RADIATION DOSE DURING PICKUP OF A RADIATION IMAGE OF A SUBJECT

BACKGROUND OF THE INVENTION

1. Field of the Invention

The invention is directed to a method for measuring the imaging dose in the framework of the pickup of a radiation image of a subject, particularly an x-ray image, whereby a radiation source is employed for generating radiation, a solid-state radiation detector is employed for image pick up, and a sensor is employed for determining the imaging dose.

2. Description of the Prior Art

In medical x-ray diagnostic installations that serve the purpose of generating radiation images and wherein the determination of the imaging dose is required in order to expose the patient under examination to only the minimally required x-radiation, an ionization chamber is employed for determining the imaging dose. This is arranged in the region of the solid-state radiation detector (with reference to the direction of the incident radiation) and should be as radiation-transparent and shadow-free as possible, so that it is not imaged thereon. The functioning of the ionization chamber is then such that, due to the x-radiation in a charged air capacitor, it generates a current usually lying in the pico-ampere range that is proportional to the dose. Measuring the pico-ampere current is difficult and is particular difficult when the ionization current drops into the femto-ampere range given employment of correspondingly low tube operating voltages. Further problems in the employment of ionization chambers are that the signal of the ionization chamber is determined by the air density in its interior, i.e., the air pressure and the temperature of the measuring chamber must be known and the chamber signal must be corrected by counter-measures in order to be able to determine the correct imaging dose.

The publication. "Bildgebende Systems fur die medizinische Diagnostik". H. Morneburg, Ed., Publicic MCD, 1995, pp. 282–283, discloses the arrangement of a semiconductor radiation detector for dose measurement behind a film cassette in which an X-ray film is arranged.

SUMMARY OF THE INVENTION

An object of the present invention is thus to provide a method as well as a corresponding apparatus with which the imaging dose can be measured in a simple way without employment of an ionization chamber and, thus, while avoiding the initially cited difficulties, given employment of a solid-state radiation detector for image pickup.

This object is inventively achieved in a method and an apparatus of the type initially described, but inventively having a radiation sensor on a semiconductor base that, with reference to the direction of the radiation incident onto the solid-state radiation detector, lies following the solid-state radiation detector, the radiation penetrating the solid-state radiation detector being measured the radiation sensor and the radiation sensor supplying an output signal that is representative of the measured radiation, and wherein the imaging dose established in front of the solid-state radiation detector is determined based on the output signal, and wherein the output signal of the radiation detector is processed dependent on the transmission behavior of the solid-state radiation detector within the framework of determining the imaging dose in front of the solid-state radiation detector.

The inventive method is based on the recognition that non-radiation-transparent semiconductor radiation detectors have been known for a short time, i.e. solid-state detectors that do not have the initially cited disadvantages in view of temperature and air density problems. The second important perception is that adequate measurable x-radiation is still present following the solid-state radiation detector, and that the absorption behavior of the solid-state radiation detector which is composed of different materials in sandwich structure can be identified exactly enough, so that conclusions can be ultimately drawn about the radiation dose incident in the illumination plane. The inventive method thus enables the creation of a completely new system that employs only solid-state detectors (the aforementioned "radiation sensor" could also be referred to as a "radiation detector," however, the term "radiation sensor" will be used herein to avoid confusion with the solid-state radiation detector which is used for detecting the radiation image). These perceptions make it possible to correspondingly process the output signal supplied by the radiation detector, for example a Si-semiconductor receiver, this output signal being a criterion for the admittedly very slight x-radiation penetrating the solid-state radiation detector, in order to determine the imaging dose. Within the framework of determining the imaging dose in front of the solid-state radiation detector, the output signal of the radiation detector can be inventively processed dependent on the transmission behavior of the solid-state radiation detector, on the spectrum of the radiation source, particularly of the x-radiator, and on the transparency of the transirradiated subject. This can ensue with an algorithm derivable therefrom, as is similarly the case given known ionization chamber systems. Differing therefrom, however, the determination ensues based on the signal measured following the solid-state radiation detector as well as taking the transmission behavior of the solid-state radiation detector into consideration. It is especially advantageously possible with the inventive method to determine the imaging dose with adequate precision independently of the external parameters to the farthest-reaching extent, whereby, further, all occlusion and transparency difficulties at the detector side are eliminated. The dependable and, above all else, very fast determination of the imaging dose particularly advantageously enables the control of the registration mode dependent on the identified imaging dose.

In conjunction therewith, it is also advantageous when the output signal of the radiation detector is processed dependent on the spectrum of the radiation source and/or on the transparency of the transirradiated subject in the framework of determining the imaging dose preceding the solid-state radiation detector. Thus, all influencing quantities can be dependable taken into consideration, as a result whereof an unnecessary radiation load on the subject is avoided and images of the transirradiated subject that can be easily diagnosed can be produced.

Within the framework of determining the imaging dose preceding the solid-state radiation detector, the output signal of the radiation detector is advantageously processed by a computer; in particular, a memory wherein data dependent on the transmission behavior and/or on the spectrum and/or on the transparency are stored is allocated to the computer for this purpose. The computer can then access these data in the determination of the imaging dose. A memory has proven advantageous wherein the data are stored in the form of a look-up table.

In addition to the above-described method, the invention is directed to an apparatus for the registration of radiation images, particularly a medical x-ray system for the implementation of the inventive method, having a radiation source, a solid-state radiation detector and a sensor for determining the image dose. In the inventive apparatus the sensor is a radiation detector on a semiconductor base for measuring the radiation penetrating the solid-state radiation detector that, with reference to the direction of the radiation incident onto the solid-state radiation detector, is arranged following the solid-state radiation detector, this sensor supplying an output signal that is representative of the measured radiation, and the imaging dose established in front of the solid-state radiation detector is determined based on the output signal.

For determining the imaging dose, a computer can be inventively provided with which the output signal of the radiation detector can be processed dependent on the transmission behavior of the solid-state radiation detector, on the spectrum of the radiation source, particularly of the x-radiator, and on the transparency of the transirradiated subject. The control of the registration mode itself can ensue dependent on the identified, imaging dose.

Since the solid-state radiation detector is several times larger than the radiation sensor, i.e. the imaging area is significantly larger than the sensor area, difficulties, for example with respect to a central arrangement of the radiation sensor with respect to the center of the solid-state radiation detector, particularly derive when a subject is to be registered that is arranged outside the center of the solid-state radiation detector. In this case, the full, unattenuated x-radiation impinges the area sampled by the sensor arranged at the back, for which reason a correspondingly high radiation dose is also measured there behind. The actual region of interest in view of the imaging dose, however, is not measured in this case. In order to also enable a dependable determination of the imaging dose in such a case, namely in the region actually of interest, it is provided according to an expedient, further embodiment of the invention that a plurality of radiation detectors are provided, these being arranged behind the solid-state radiation detector in the form of a matrix or an array. This embodiment of the invention makes it possible to undertake local dose measurements, so that only the region of interest is in fact measured and an exact determination of dose is possible. The radiation detectors are thereby inventively arranged at the same distance with respect to the solid-state radiation detector, so that problems arising from different spacings that disadvantageously influence the incident photon flux density are eliminated.

DESCRIPTION OF THE PREFERRED EMBODIMENTS

Figure 5:
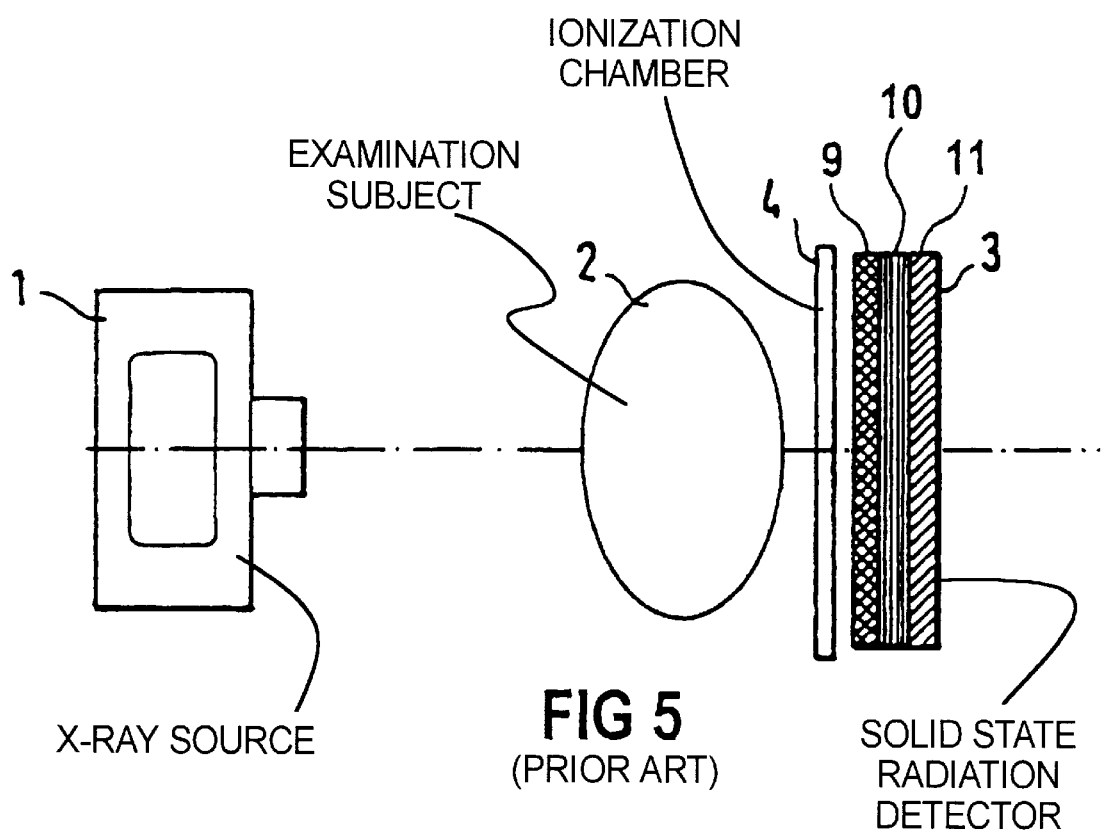
FIG. 5 is a schematic illustration of a conventional x-ray image pick up system.
Figure 6:
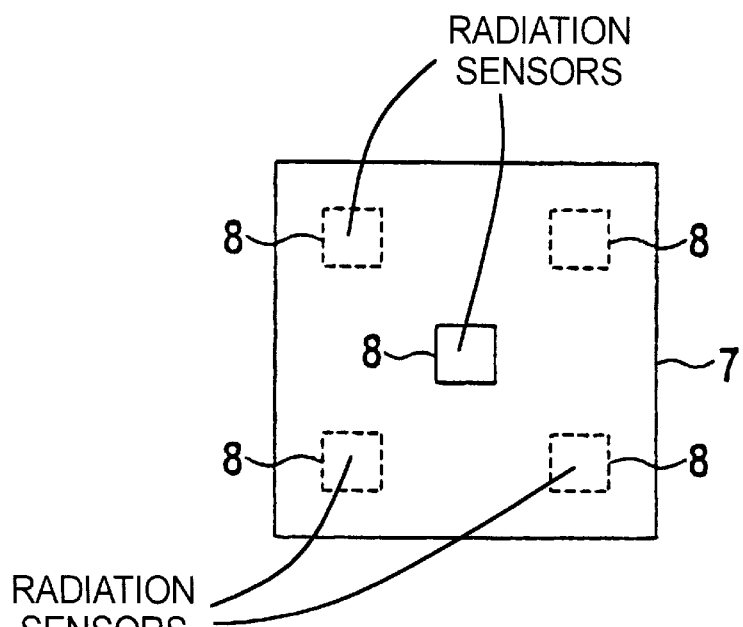
FIG. 6 is a back view of the solid-state radiation detector according to FIG. 1.

The structure according to FIG. 5, which reflects the prior art, will first be explained in brief. The arrangement comprises an x-radiator 1 in whose radiation region a subject 2 is arranged. A solid-state radiation detector 3 that serves for the registration of the radiation image follows this. A transparent ionization chamber 4 is arranged between the subject 2 and the solid-state radiation detector 3, this ionization chamber 4 supplying an output signal that is representative of the x-radiation incident onto the solid state radiation detector 3 for determining the imaging dose from an output signal, which is subsequently post-processed. The arrangement of the ionization chamber in the image region of the solid-state radiation detector leads to slight occlusions, for which reason high demands are made of the transparency of the ionization chamber. Further disadvantages are the dependency of the supplied output signal on the air pressure and on the temperature of the ionization chamber, which must be correspondingly corrected within the framework of the post-processing.

Figure 1:
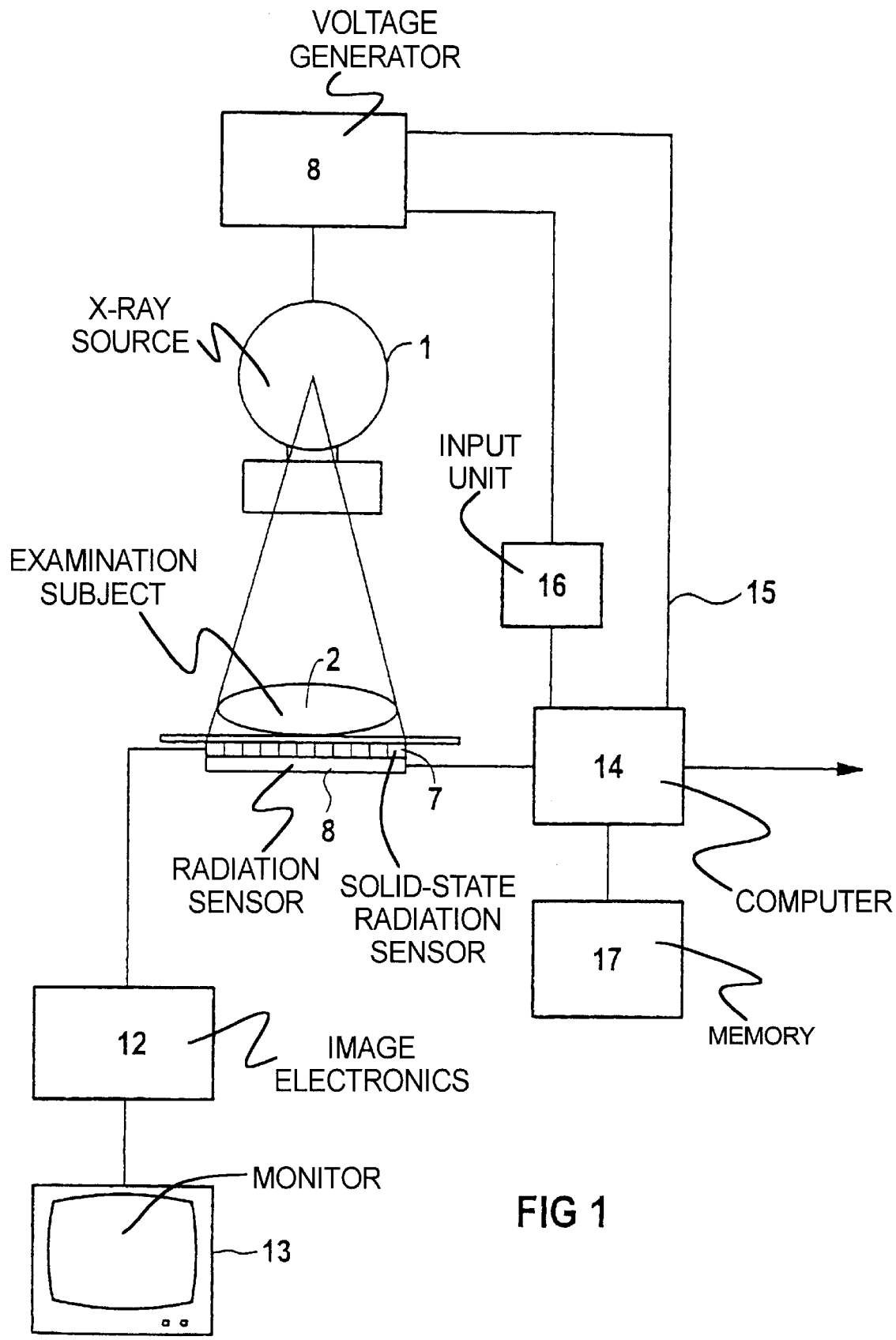
FIG. 1 is a schematic illustration of an inventive apparatus.

This contrasts with the inventive structure as shown in FIG. 1. This also has an x-radiator 5, a subject 6 lying in the radiation region thereof and a solid-state radiation detector 7 immediately following the subject 6. A sensor in the form of a radiation detector 8 on a semiconductor base is arranged behind the solid-state radiation detector 7, a Si measuring cell in the illustrated exemplary embodiment; for simplicity, this is centered with respect to the solid-state radiation detector 7. The solid-state radiation detector 7 can be composed of a matrix of detector elements, particularly on the basis of amorphous, hydrated silicon. However, it is also possible to fashion this of a scintillator with following semiconductor detectors, potentially upon intervention of a light conductor. The output signals of the solid-state radiation detector 7 are supplied to a following image electronics 12 that generates an image of the transirradiated region of the subject 6 that is played back on a monitor 13. FIG. 1 also shows that the output signals of the radiation detector 8 are supplied to a computer 14. At its input 15, the computer 14 receives signals that correspond to the x-ray spectrum of the x-radiator 1 and from which adjustable exposure data are derived. The data corresponding to the patient thickness are input via an input means 16. Corresponding characteristics are stored in the input means 16, taking the respectively set exposure data into consideration. The computer 10 operates according to an algorithm that determines the imaging dose or dose power from the output signal of the radiation detector 8. A memory 17 in which data corresponding to the transmission behavior of the solid-state detector and/or to the spectrum of the radiation source, particularly of the x-radiator, and/or to the transparency of the transirradiated subject are stored can thereby be allocated to the computer.

The functioning of the method or of the apparatus is such that the x-radiation emitted by the x-radiator 5 penetrates the subject 6, is attenuated thereat as a consequence of the radiation absorption, and impinges the surface of the solid-state radiation detector 7, generating the radiation image. The conversion of the x-ray quanta into corresponding electrical signals ensues thereat, these being read out and processed in the framework of the image processing. An admittedly slight part of the x-radiation, however, penetrates through the solid-state radiation detector 7 and can be measured with the radiation detector 8. This then supplies the output signal that is further-processed for determining the imaging dose. As the schematic illustration of the solid-state radiation detector 7 shows, this is composed of different layers 9, 10, 11 of material, but, for example, more than thee different layers or materials can also be utilized (for example, housing material or the like). This means that the sandwich-structured solid-state radiation detector 7 represents a mixture of substances that partially absorbs the x-radiation that penetrates and passes through, i.e. is critical for the x-radiation that emerges and that is measurable by the radiation detector 8.

Figure 2:
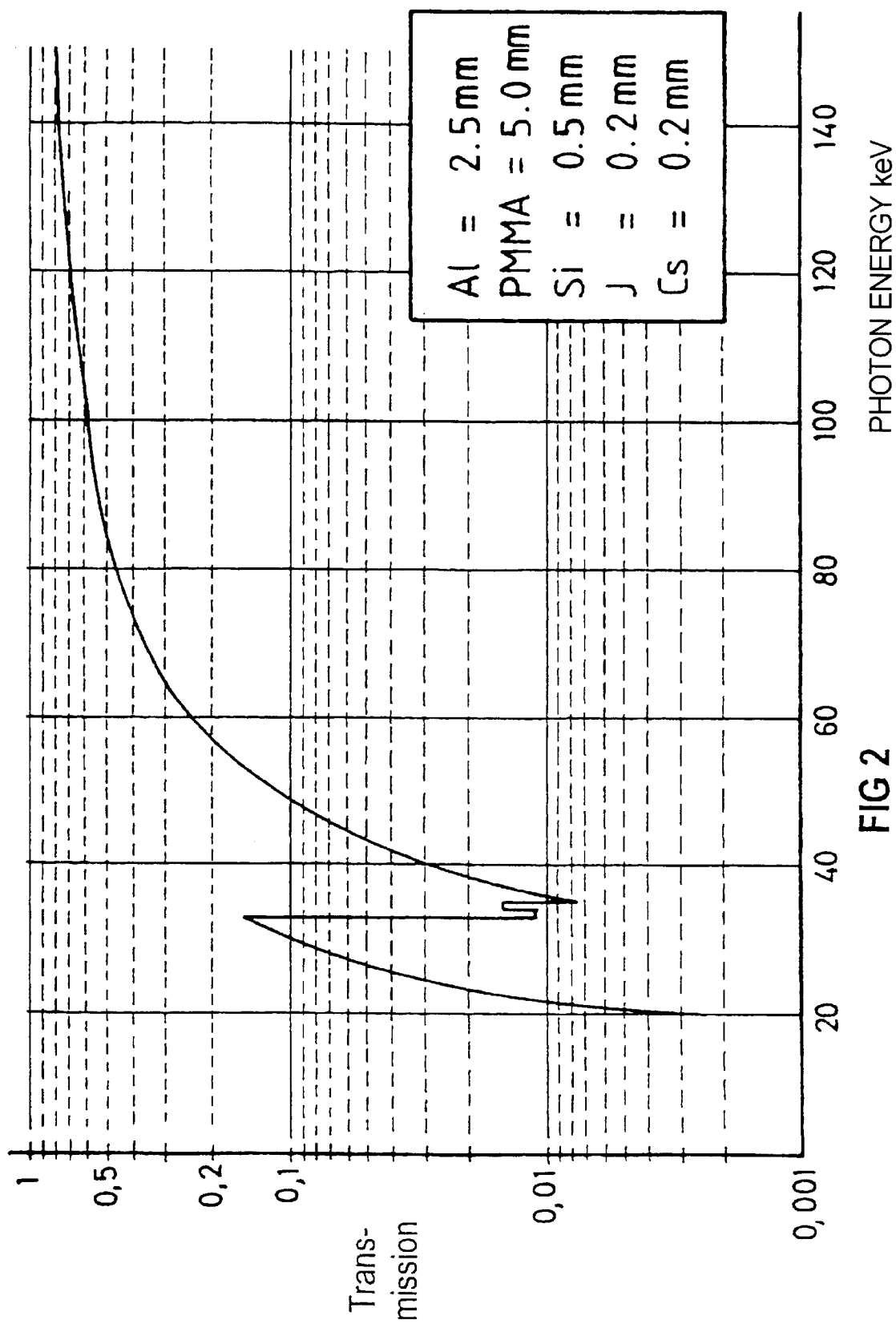
FIG. 2 illustrates a calculated transmission spectrum for a solid-state radiation detector.

Since the imaging dose in front of the solid-state radiation detector 7 is to be determined, the actual imaging dose at the opposite side of the solid-state radiation detector 7 must be discovered computationally based on the output signal of the radiation detector 8. To this end, it is first necessary to determine the transmission behavior of the solid-state radiation detector 7. FIG. 2 shows a calculated transmission profile of such a radiation detector 7. It is assumed in this profile that the radiation detector is composed of the following elements that determine its absorption behavior:
an aluminum housing (Al)
a layer carrier of plastic (PMMA)
the semiconductor Si
the scintillation layer composed of the elements J and Cs.

The individual layers or elements are present in the following thickness:
Al: 2.5 mm
PMMA: 5.0 mm
Si: 0.5 mm
J: 0.2 mm
Cs: 0.2 mm.

Taking the mass attenuation coefficients with reference to the photon energy, which are known, into consideration, the transmission curve with reference to the photon energy that is shown in FIG. 2 derives. As can be seen, the degree of transmission, which is logarithmically entered, increases proceeding from the soft radiation given low photon energies and reaches a first maximum in the region of approximately 33 keV, after which the degree of transmission clearly drops. This is because the two elements J and Cs have strong absorption bands at these energies, this being expressed in a clear discontinuity of the respective mass attenuation coefficients for the two elements. The degree of transmission rises continuously in the range of higher photon energies, as can be seen with reference to FIG. 2.

Figure 3:
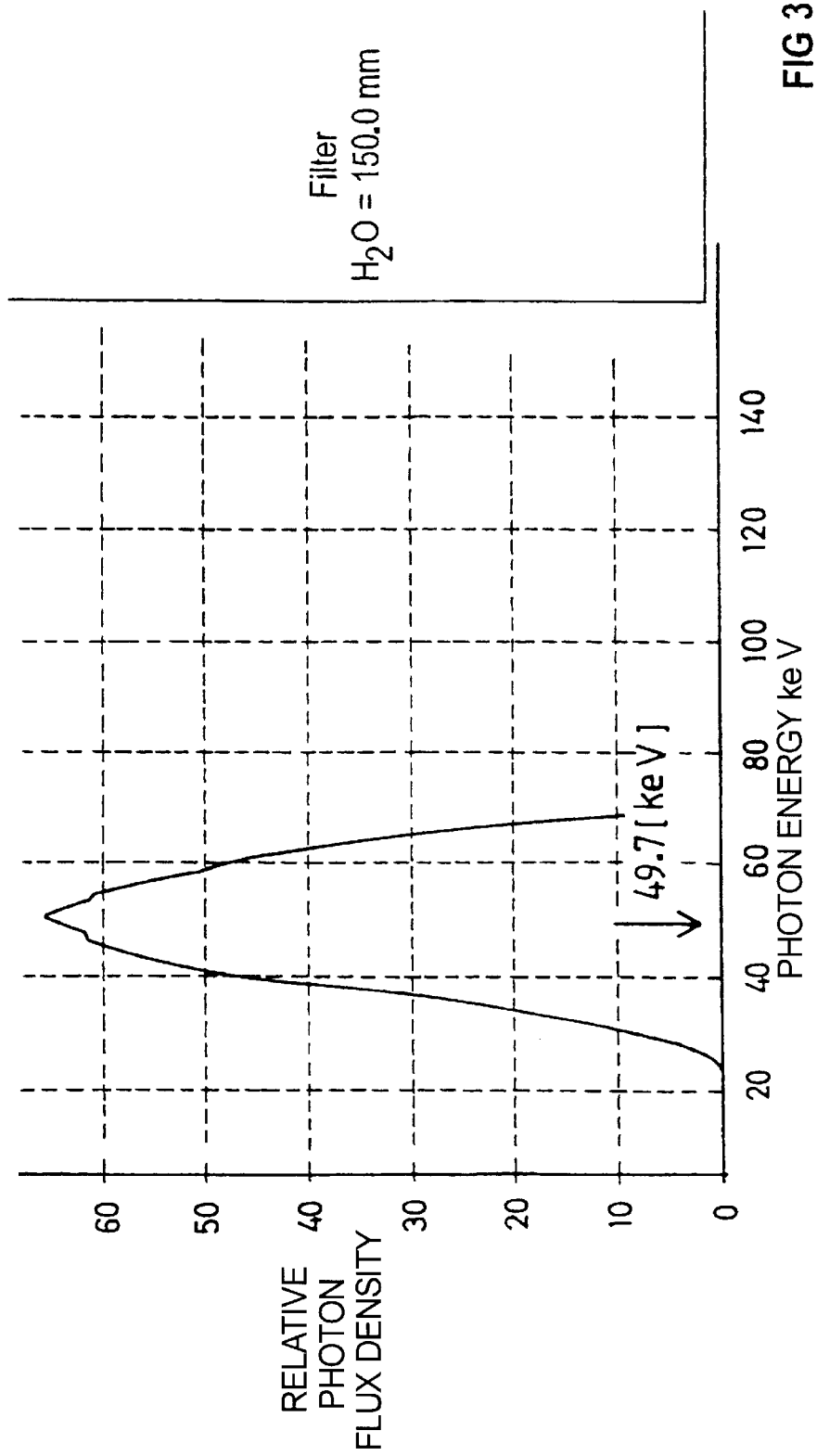
FIG. 3 illustrates a calculated quantum spectrum given employment of an ionization chamber.
Figure 4:
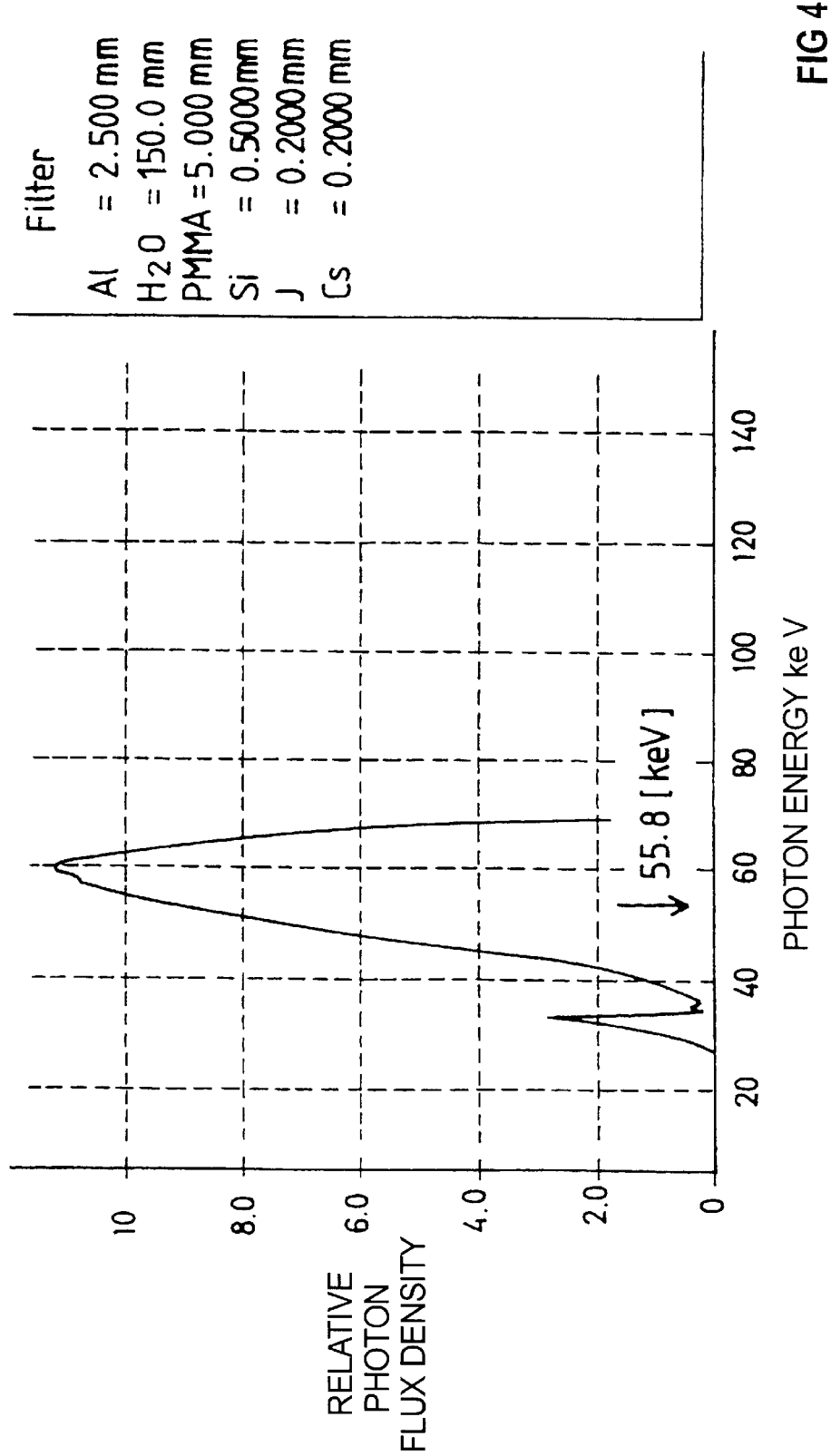
FIG. 4 illustrates a calculated quantum spectrum given employment of an inventive radiation sensor on a semiconductor base based on the transmission behavior of the solid-state radiation detector according to FIG. 2.

FIGS. 3 and 4 show two quantum spectra, whereby FIG. 3 shows a calculated quantum spectrum that can be registered with an ionization chamber, and FIG. 4 shows a calculated quantum spectrum that can be registered with the inventive radiation detector on a semiconductor base based on the absorption behavior shown in FIG. 2. The two calculations are based on a tube voltage of 70 kV and 10 mA. The relative photon flux density is entered along the ordinate; the photon energy is entered in keV along the abscissa. The calculation according to FIG. 3 is based on the assumption of a water filter, which represents the subject, having a diameter of 150 mm. The dose power that can be identified in this case, as derives from the illustrated curve whose center of gravity lies at 49.7 keV, computationally amounts to 713 $\mu$R/sec (=6.23 $\mu$Gy/sec). Based on this behavior, the imaging dose can then be calculated and the installation can be correspondingly controlled.

This is compared to the quantum spectrum shown in FIG. 4 given an inventive apparatus or, respectively, given application of the inventive method. Here, too, the relative photon flux density is entered along the ordinate and the photon energy in keV is entered along the abscissa. In addition to the solid-state radiation detector acting as filter having the aforementioned properties, a water filter having a thickness of 150 mm is also assumed here. The calculation of the spectrum ensued based on the transmission behavior to be seen from FIG. 2. In accord therewith, a first peak occurs at a photon energy of approximately 33 keV, this corresponding to the first transmission maximum shown in FIG. 2. Subsequently, the flux density again increases corresponding to the increasing degree of transmission. The center of gravity here lies at 55.8 keV. The dose power which thereby is computationally obtained amounts to 68.6 $\mu$R/sec (=600 $\mu$Gy/sec). This value only amounts to approximately 10% of the value measurable preceding the solid-state radiation detector with the ionization chamber but can be adequately precisely determined with the solid-state sensor. Based on the known transmission behavior and on the x-radiator parameters as well as on the transparency of the examination subject, the imaging dose which exist in front of the solid-state radiation detector can be determined based on the obtained output signal and corresponding operations can be performed on the system operation in controlling fashion when a predetermined maximum dose is reached.

Although modifications and changes may be suggested by those skilled in the art, it is the intention of the inventor to embody within the patent warranted hereon all changes and modifications as reasonably and properly come within the scope of his contribution to the art.

What is claimed is:

1. A method for measuring an imaging radiation dose, comprising the steps of:
    emitting radiation from a radiation source, said radiation propagating in a propagation direction;
    detecting said radiation with a solid-state radiation detector which allows said radiation to penetrate therethrough and which has a transmission behavior which influences the radiation penetrating through said solid-state radiation detector;
    disposing a radiation sensor, comprised of a radiation detector on a semiconductor base, behind said solid-state radiation detector in said propagation direction, and detecting the radiation penetrating through said solid-state radiation detector with said radiation sensor and generating an output signal from said radiation sensor dependent thereon; and
    processing said output signal in a computer dependent on the transmission behavior of said solid-state radiation detector to determine an imaging radiation dose at a location in front of said solid-state radiation detector.

2. A method as claimed in claim 1 wherein said radiation has a radiation spectrum and comprising processing said output signal also dependent on said radiation spectrum to determine said imaging radiation dose.

3. A method as claimed in claim 1 comprising disposing an examination subject, having a radiation transparency, between said radiation source and said solid-state radiation detector, and comprising processing said output signal also dependent on said radiation transparency to determine said imaging radiation dose.

4. A method as claimed in claim 1 wherein said radiation has a radiation spectrum, and comprising disposing an examination subject, having a radiation transparency, between said radiation source and said solid-state radiation detector, and comprising processing said output signal in said computer dependent on said transmission behavior, said radiation spectrum and said radiation transparency to determine said imaging radiation dose.

5. A method as claimed in claim 1 wherein said radiation has a radiation spectrum, and comprising disposing an examination subject having a radiation transparency, between said radiation source and said solid-state radiation detector, and comprising storing data in a memory in said computer representing at least one of said transmission behavior, said radiation spectrum and said transparency, and processing said output signal in said computer using said data to determine said imaging radiation dose.

6. A method as claimed in claim 1 comprising disposing an examination subject between said radiation source and said solid-state detector and obtaining an image of said examination subject using said solid-state radiation detector, and comprising the additional step of controlling obtaining said image dependent on said imaging radiation dose.

7. An apparatus as claimed in claim 1 wherein said apparatus is adapted to receive an examination subject between said radiation source and said solid-state radiation detector for obtaining an image of said examination subject from radiation from said x-ray source attenuated by said examination subject and detected by said solid-state radiation detector, and wherein said computer controls obtaining said image dependent on said imaging radiation dose.

8. An apparatus as claimed in claim 1 wherein said radiation sensor is a first radiation sensor, and further comprising a plurality of additional radiation sensors, said first radiation sensor and said plurality of additional radiation sensors all being disposed behind said solid-state radiation detector in said propagation direction.

9. An apparatus as claimed in claim 8 wherein said first radiation sensor and said plurality of additional radiation sensors are disposed in a matrix.

10. An apparatus as claimed in claim 8 wherein said first radiation sensor and said plurality of additional radiation sensors are disposed in an array.

11. An apparatus as claimed in claim 8 wherein said first radiation sensor and said plurality of additional radiation sensors are all respectively disposed at a same distance behind said solid-state radiation detector in said propagation direction.

12. An apparatus for measuring an imaging radiation dose, comprising:

a radiation source which emits radiation propagating in a propagation direction;

a solid-state radiation detector disposed in said radiation, which allows said radiation to penetrate therethrough and which has a transmission behavior which influences the radiation penetrating through said solid-state radiation detector;

a radiation sensor disposed behind said solid-state radiation detector in said propagation direction, said radiation sensor comprising a radiation detector on a semiconductor base, and said radiation sensor detecting the radiation penetrating through said solid-state radiation detector and generating an output signal dependent thereon; and a computer supplied with said output signal for processing said output signal dependent on said transmission behavior to determine an imaging radiation dose at a location in front of said solid-state radiation detector.

13. An apparatus as claimed in claim 12 wherein said radiation has a radiation spectrum, and wherein said computer determines said imaging radiation dose also dependent on said radiation spectrum.

14. An apparatus as claimed in claim 12 which is adapted to receive an examination subject, having a radiation transparency, between said radiation source and said solid-state radiation detector, and wherein said computer determines said imaging radiation dose also dependent on said transmission behavior.

15. An apparatus as claimed in claim 12 wherein said radiation has a radiation spectrum, and wherein said apparatus is adapted to receive an examination subject, having a radiation transparency, between said radiation source and said solid-state radiation detector, and wherein said computer determines said imaging radiation dose dependent on said transmission behavior, said radiation spectrum and said radiation transparency.

16. An apparatus as claimed in claim 12 wherein said radiation has a radiation spectrum, and wherein said apparatus is adapted to receive an examination subject, having a radiation transparency, between said radiation source and said solid-state radiation detector, and wherein said computer comprises a memory for storing data representing at least one of said transmission behavior said radiation spectrum and said radiation transparency, and wherein said computer determines said imaging radiation dose dependent on said data.

\* \* \* \* \*